(12) United States Patent
Najdeni

(10) Patent No.: US 9,821,110 B2
(45) Date of Patent: Nov. 21, 2017

(54) SYSTEMS AND METHODS FOR MINIMIZING LOSS OF CELLULAR COMPONENTS DURING APHERESIS

(71) Applicant: FENWAL, INC., Lake Zurich, IL (US)

(72) Inventor: Gert Najdeni, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 313 days.

(21) Appl. No.: 14/050,948

(22) Filed: Oct. 10, 2013

(65) Prior Publication Data

US 2015/0101994 A1   Apr. 16, 2015

(51) Int. Cl.
  *A61M 1/36*   (2006.01)
  *A61M 1/34*   (2006.01)
  *B01D 61/24*   (2006.01)

(52) U.S. Cl.
  CPC .......... *A61M 1/367* (2013.01); *A61M 1/3496* (2013.01); *B01D 61/243* (2013.01)

(58) Field of Classification Search
  CPC .... A61M 1/3496; A61M 1/367; B01D 61/243
  See application file for complete search history.

(56) References Cited

U.S. PATENT DOCUMENTS

| | | | |
|---|---|---|---|
| 5,194,145 A * | 3/1993 | Schoendorfer | A61M 1/3496 210/321.63 |
| 2005/0051486 A1 | 3/2005 | Zuk, Jr. | |
| 2005/0137516 A1 | 6/2005 | Min et al. | |
| 2014/0199680 A1* | 7/2014 | Min | A61M 1/3472 435/2 |

FOREIGN PATENT DOCUMENTS

| | | |
|---|---|---|
| WO | WO91/17809 A1 | 11/1991 |
| WO | WO2013/043433 A2 | 3/2013 |

OTHER PUBLICATIONS

European Patent Office Search Report, dated Jan. 27, 2015, Place of Search: The Hague, Application No. 13189811.6, Applicant: Fenwal, Inc.

\* cited by examiner

*Primary Examiner* — John Kim
(74) *Attorney, Agent, or Firm* — Cook Alex Ltd.

(57) ABSTRACT

Systems and methods for processing a fluid including a suspension of biological cellular components are disclosed including a single-use kit comprising a container for the fluid; a separation device for retaining selected biological cellular components and allowing other biological cellular components of said fluid to pass therethrough; a flow path connecting the container to the separation device, the container being configured, when in use, to be positioned so that gravity tends to flow fluid through the flow path. The flow path has a segment in close proximity to the container with a configuration including a positive slope, so that biological cellular components moving through the segment are subjected to a gravitational force tending to impede movement through the flow path segment. The flow path segment preferably has a generally circular configuration, and a diameter of approximately 1.5 inches. Alternatively, the flow path segment may have a generally S-shaped configuration.

12 Claims, 4 Drawing Sheets

SYSTEMS AND METHODS FOR MINIMIZING LOSS OF CELLULAR COMPONENTS DURING APHERESIS

FIELD OF THE DISCLOSURE

Background of the Invention

The present application is related to systems and methods for performing apheresis procedures, and, more particularly to systems and methods for minimizing the loss of desired cellular material and the potential for clogging or fouling in the case of membrane separation.

Apheresis is a medical procedure in which the blood of a donor or patient is passed through an apparatus that separates out one or more of the cellular components (such as plasma, red blood cells, leukocytes and platelets). Separation of the cellular components is commonly accomplished by centrifugation, based on the difference in density of the cellular components, or by membrane separation, based on the particle size. In either instance, a single use fluid circuit or kit is used in conjunction with a hardware component, with the kit typically including a source container, containing the whole blood or other biological fluid to be processed, connected (or connectable) to a fluid flow path, typically defined by a tubing, to the separator device, which, in turn, is connected to a flow path to a product container for receiving the desired cellular component. The hardware component typically comprises a plurality of pumps, valves and/or clamps for controlling flow through the kit, and a controller for operating the same.

When the kit is mounted to the hardware component, source and product containers are typically suspended from weight scales, with the tubings connected to the source and product containers routed vertically downwards and then directed generally laterally toward the separator device, which is mounted to the face of the hardware component. If during an apheresis procedure, the procedure requires intermittent flow (e.g., to test samples for cell count viability, etc.) or is otherwise interrupted, and the source and/or product containers are left un-agitated for a period of time, heavier cellular material will separate out and settle in the vertical portions of the tubing connected to the containers. The settled cellular material in the tubings cannot be recovered back into the containers, and may thus be permanently lost (if settled from the tubing connected to the product container) or cause a high concentration of cellular material to reach the separator device upon resumption of the procedure that could create unexpected pressure changes in the system and clogging of the separator.

By way of the systems and methods disclosed herein, a solution to the foregoing problems is provided.

SUMMARY OF THE INVENTION

In a first aspect of the present disclosure, a single-use fluid circuit for processing a fluid including a suspension of biological cellular components is provided comprising a container for the fluid; a separation device for retaining selected cellular components and allowing other cellular components of said fluid to pass therethrough; and a flow path connecting the container to the separation device. The container is configured, when in use, to be positioned so that gravity tends to cause cellular that settles out of suspension to flow into the flow path. The flow path comprises a segment in close proximity to the container with a configuration including an upward or positive slope, so that cellular components moving through the segment are subjected to a gravitational force tending to impede movement through the flow path segment.

In another aspect, the flow path segment of the fluid circuit has a generally circular configuration, and preferably has a diameter of approximately 1.5 inches. As an alternative, the flow path segment may have a generally S-shaped configuration.

In a further aspect, configuration of the flow path segment may be maintained by an adhesive. As an alternative, the configuration of the flow path segment may be maintained by a clamp.

In another aspect, the single-use fluid circuit may comprise an access site for connecting the flow path to the collection container, with the flow path segment being connected directly, or otherwise as close as possible, to the access site.

In a second aspect of the disclosure, a method is provided for reducing the accumulation of cellular material in the tubing during time periods when a procedure for processing a fluid including a suspension of biological cellular components utilizing a single use fluid circuit comprising a container for the fluid connected by a flow path to a separation device is interrupted. The method comprises providing a segment of the flow path in close proximity to the container with a positive slope, so that cellular components moving through the segment are subjected to a gravitational force tending to impede movement through the tubing segment toward the separation device. In related aspects, the flow path segment is provided with the configurations as set forth above.

In a third aspect, the present disclosure provides a system for processing biological fluids including cellular components comprising a single-use kit comprising a container for the biological fluid, a separation device, and a flow path providing fluid communication between the container and the separation device; a reusable hardware component for selectively flowing the biological fluid between the container and the separator; with the flow path further comprising having a segment in close proximity to the container with a configuration including a positive slope, so that biological cellular components moving through the segment are subjected to a gravitational force tending to impede movement through the flow path segment.

In any of its aspects, the separator may comprise a membrane separator, and, more specifically, a spinning membrane separator.

DETAILED DESCRIPTION

A more detailed description of the systems and methods in accordance with the present disclosure is set forth below.

It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
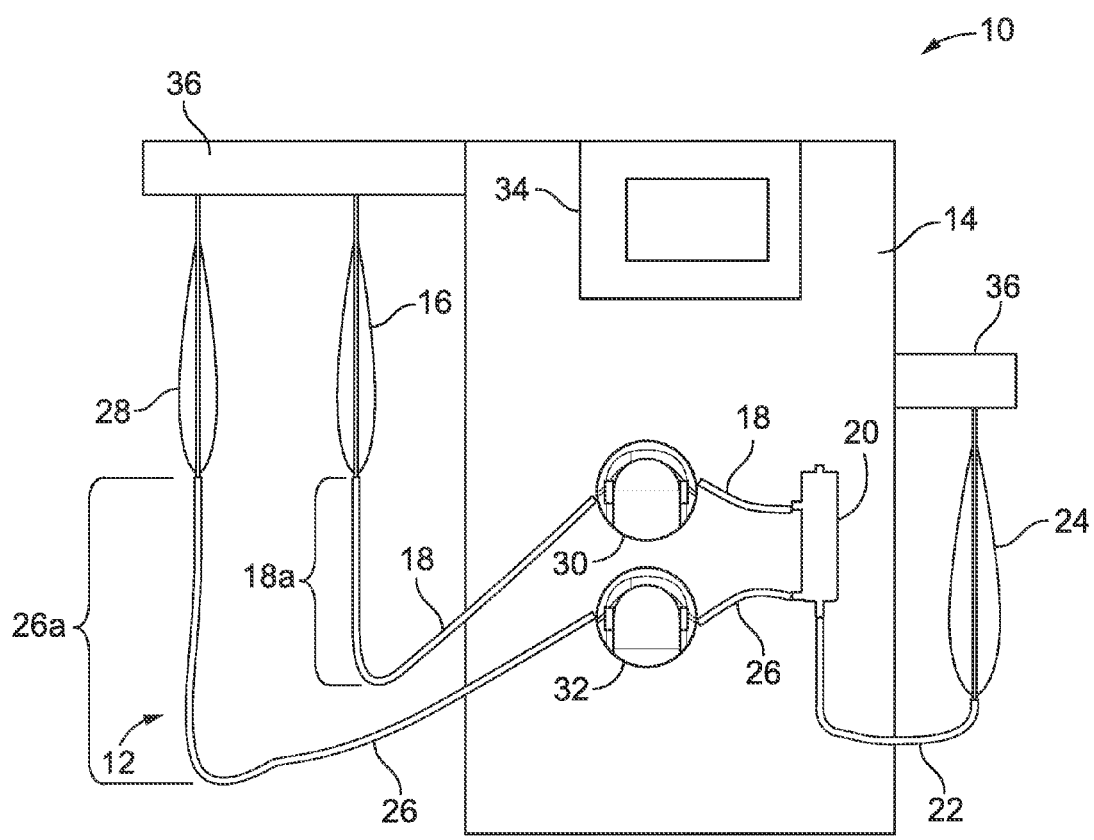
FIG. 1 is a schematic representation of a prior art apheresis system including a single-use fluid processing kit and a durable hardware component.

Turning to FIG. 1, there is seen a schematic representation of a typical apheresis system 10 comprising a single-use fluid processing kit 12 and a durable hardware component 14. The system 10 is particularly well suited to processing whole blood and/or other suspensions of biological fluids. By way of example and not limitation, the systems and methods described herein are particularly suited for a the processing of mononuclear cells (MNC), during which the MNCs separated from the fluid in which they are suspended for further processing before administering to a patient. One example of a system and method in which the subject matter of the present disclosure may be used is described in WO 2013/043433, the contents of which is incorporated herein by reference. It is understood, however, that the use systems and methods described herein are not limited to such procedures and that the systems and methods may be advantageously utilized in connection with other apheresis procedures.

As illustrated, the fluid processing kit 12 includes a source container 16 connected by tubing 18 to define a flow path to the inlet of a separation device 20. The separation device is preferably a membrane separator, and, more preferably a spinning membrane separator. Alternatively, the separation device may comprise a chamber that is part of a centrifugal separator.

A detailed description of a spinning membrane separator may be found in U.S. Pat. No. 5,194,145 to Schoendorfer, which is incorporated by reference herein. This patent describes a membrane-covered spinner having an interior collection system disposed within a stationary shell. The membrane separator includes two outlets. One outlet is connected by tubing 22 to define a flow path to a container 24 for receiving the filtrate, which is typically considered waste. The second outlet is connected by tubing 26 to define a flow path to a container 28 for receiving the precipitate, which is typically the desired cellular component and the final product of the apheresis procedure.

The durable hardware component 14 preferably includes one or more flow controlling devices, such as, for example, pumps, such as peristaltic or diaphragm pumps, generally indicated at 30 and 32, that are preferably respectively associated with the tubings 18 and 26 for controlling fluid flow of the fluid suspension from the source container 16 to the membrane separator 20 and the flow of the precipitate from the membrane separator to the final product container 28. Other types of flow controlling devices may also be used as controllers, including but not limited to gravity-controlled flow controllers. The durable hardware component 14 also typically includes a programmable controller 34 employing a programmable microprocessor, a drive system (not shown) for the membrane separator 20 (if the separator 20 is a spinning membrane separator), and hangers 36, typically including weight scales, from which the various containers 16, 24 and 28 are suspended, with their respective tubings 18, 22 and 26 being routed vertically downwards.

As noted above, the processing of MNCs, as well as other biological fluids, is often a discontinuous process, with the source and product containers being left un-agitated for a period of time. During this time, the MNCs will tend to settle out of suspension and out of the containers 18 and 26 into the vertical portions 18a and 26a of the tubings 18 and 26.

If the MNCs settle into the vertical portion 18a of the tubing 18 from the source container 16, upon resumption of the membrane separation, a high concentration of MNCs will initially reach the membrane separator, potentially exceeding its filtration capacity and resulting in clogging or fouling of the membrane.

If, during a pause in the processing to permit, e.g., samples of the separated MNCs to be taken from the product container 28 and analyzed for cell counts, viability, etc., the MNC's in the product container 28 that settle into the vertical portion 26a of the tubing 26 cannot be recovered and must be treated as waste, as they cannot be pumped back into the product container due to tightly-controlled processing protocols.

By way of the present disclosure, the fluid processing kit is provided with a configuration that minimizes the amount of cellular components that may settle out of the container containing the suspension. More particularly, the flow path from either or both the source container and product container is provided with a segment in close proximity to the container that has a configuration including a positive slope, i.e., point in an upward direction, so that cellular components moving through the segment are subjected to a gravitational force tending to impede movement through the flow path segment, thus limiting the amount of cellular material settling in the flow path.

Figure 2:
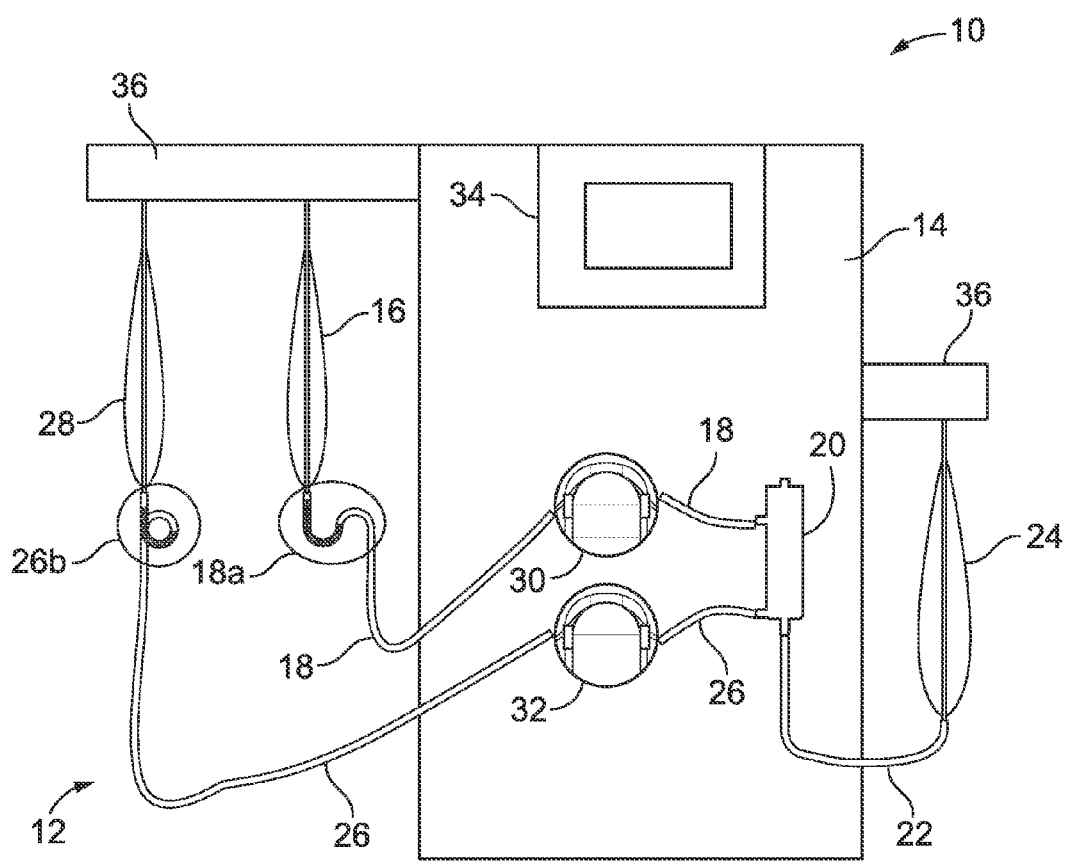
FIG. 2 is a schematic representation of an apheresis system including a single-use fluid processing kit and a durable hardware component in accordance with the present disclosure.
Figure 3:
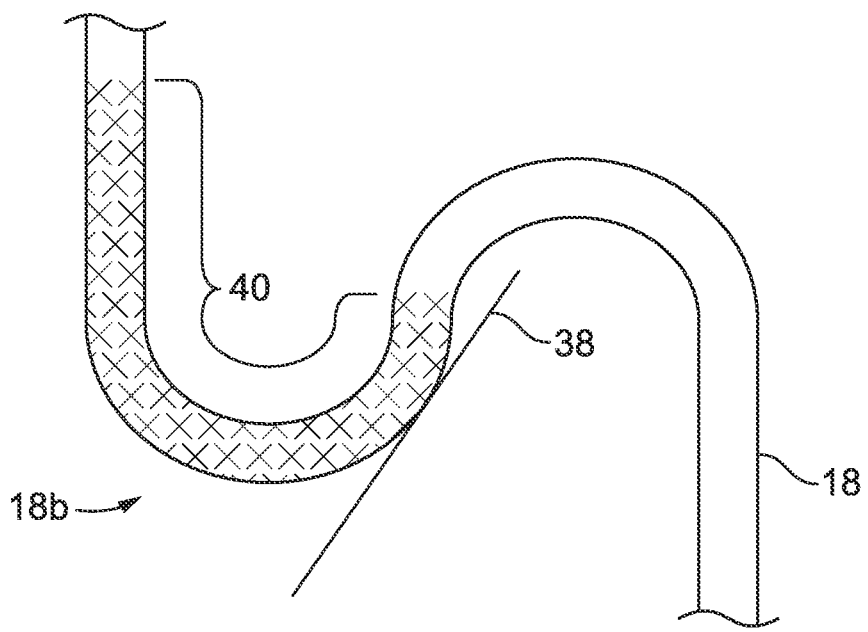
FIGS. 3 and 4 are enlarged fragmentary views of a portion of the tubing comprising the single-use fluid processing kit shown in FIG. 2.

With reference to FIG. 2, in which elements common to FIG. 1 are, provided with like reference numerals, the flow paths defined by the tubings 18 and 26 are provided with segments adjacent their associated containers that include an upward or positive slope. The closer the positively-sloped tubing segment is to the point of attachment of the tubing to the container, the lesser the amount of cellular material that settles out of the suspension will accumulate in the tubing. As examples, the positive-sloping segment of tubing 18 may be provided with an S-shaped configuration 18b. Alternatively, the positive-sloping segment of tubing may have a looped or circular configuration, in which the tubing segment 26 has a circular configuration 26b. The tubing segments 18b and 26b are better seen in FIGS. 3 an 4, respectively, where the positive-slope for the segments is indicated by the diagonally-oriented lines 38, and the settled cellular material is represented by the shading 40.

Figure 4:
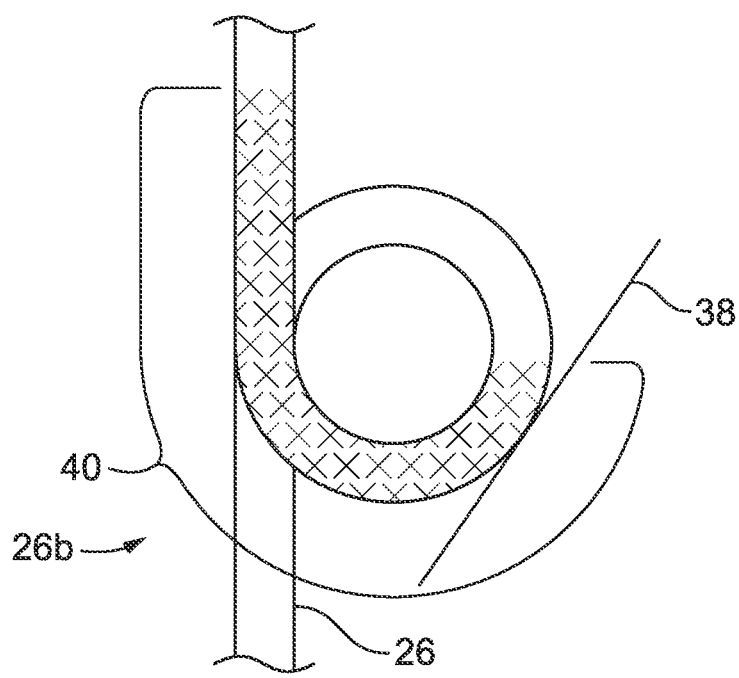

The positively-sloped segment of the tubing may be maintained by, e.g. an adhesive that secures the overlapping portions the looped tubing configuration (FIG. 4) to each other. Alternatively, a clamp or clip may be employed, as described in greater detail below in connection with FIGS. 5 and 6. As a further alternative, the tubing segment may be thermoformed to maintain its desired configuration.

Figure 6:
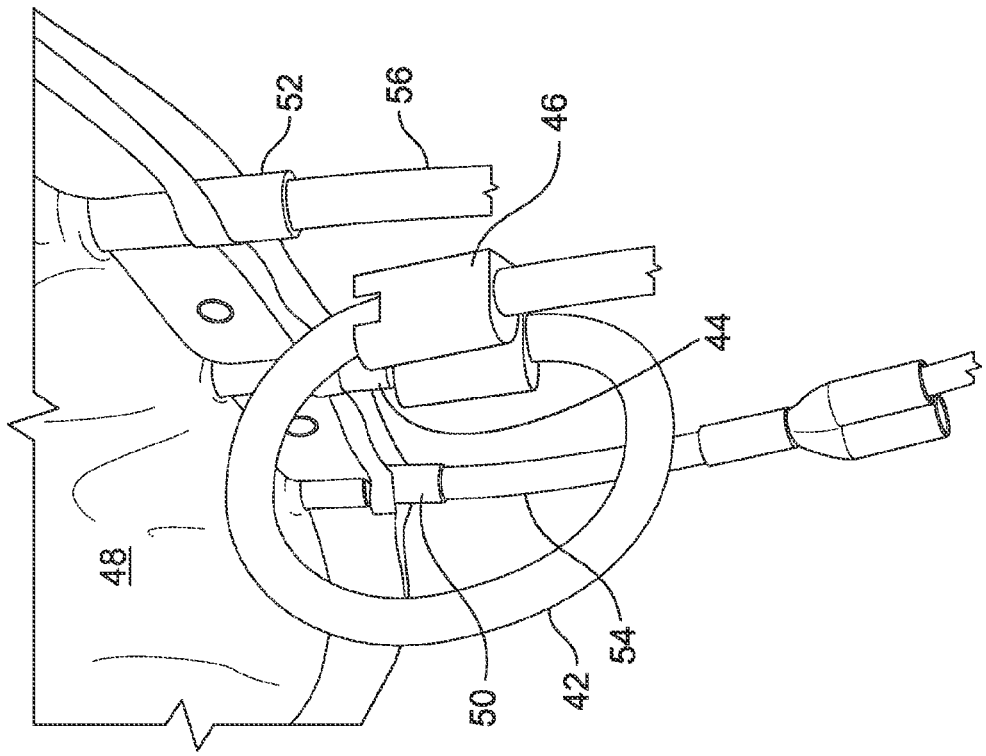
FIGS. 5 and 6 are alternate embodiments of the tubing configuration shown in FIG. 3.
Figure 5:
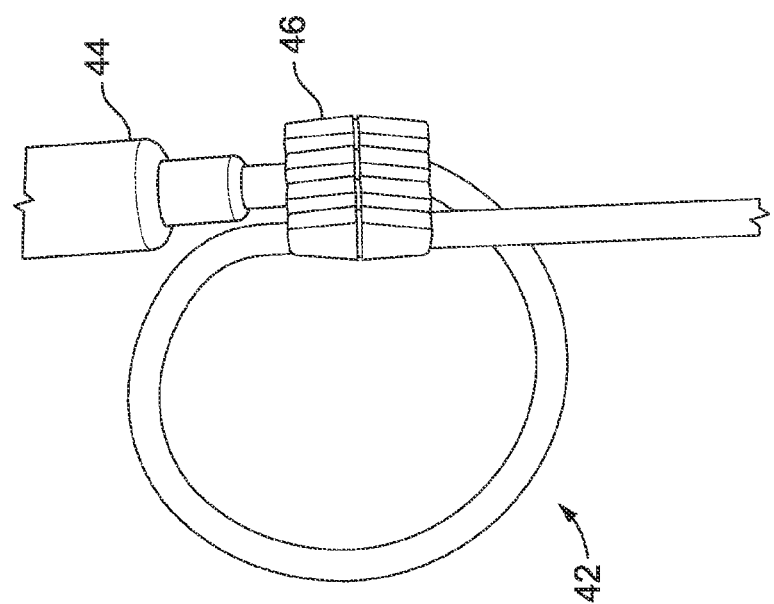

The containers 16 and 28 are typically flexible plastic pouches or bags formed of opposed sheets sealed together at their peripheral edges with a port or tube positioned between the sheets to provide access to the interior, with the tubing, such as tubing 18 and 26, being secured to the port. With reference to FIG. 5, a looped tubing segment 42 is seen connected to and extending from an access port 44 that is associated with a peripheral edge of a pouch (not seen). A clip 46 maintains the looped or circular configuration of the tubing segment 42 by engaging the overlapping portions of the tubing. The clip 46 is located on the tubing segment 42 in close proximity to the access port 44 in order to minimize the amount of tubing into which cellular components may settle. FIG. 6 discloses a flexible container 48 having a looped tubing segment 42 and port 44 arrangement similar to FIG. 5, with the clip 46 for maintaining the configuration in abutment with the access port. The container 48 also includes auxiliary ports 50, 52 having tubing segments 54 and 56 associated therewith to provide access to the interior of the container to, e.g., draw samples, infuse a treatment solution, etc.

Thus, systems and methods for minimizing loss of cellular components during apheresis have been disclosed having several aspects.

In a first aspect of the disclosure, a single-use fluid circuit for processing a fluid including a suspension of biological cellular components is provided that comprises a container for the fluid; a separation device for retaining selected biological cellular components and allowing other biological cellular components of said fluid to pass therethrough; a flow path connecting the container to the separation device, with the container being configured, when in use, to be positioned so that gravity tends to flow fluid through the flow path. The flow path includes a segment in close proximity to the container having a configuration including a positive slope, so that biological cellular components moving through the segment are subjected to a gravitational force tending to impede movement through the flow path segment.

In a second aspect of the disclosure, a procedure for processing a fluid including a suspension of biological cellular components is disclosed that utilizes a single use fluid circuit comprising a container for the fluid connected by a flow path to a separation device, the flow path being configured to be selectively draw fluid through the tubing, a method for reducing the accumulation of cellular material in the tubing during time periods when the procedure is interrupted. The method comprises providing a segment of the flow path in close proximity to the container with a positive slope, so that cellular components moving through the segment are subjected to a gravitational force tending to impede movement through the tubing segment toward the separator.

In a third aspect, a system for processing biological fluids including cellular components is provided that comprises a single-use kit having a container for the biological fluid, a separation device, and a flow path providing fluid communication between the collection container and the membrane separator. The system further includes a reusable hardware component for selectively flowing the biological fluid between the container and the separator, and the flow path further comprises a segment in close proximity to the container having a configuration including a positive slope, so that biological cellular components moving through the segment are subjected to a gravitational force tending to impede movement through the flow path segment.

In any of its aspects, the flow path segment may have a generally circular configuration or, alternatively, a generally S-shaped configuration; the configuration of the flow path segment may be maintained by an adhesive or, alternatively, the configuration of the flow path segment may be maintained by a clamp; and/or the fluid circuit may further comprising an access port for connecting the flow path to the collection container, with the flow path segment being connected adjacent to the access port. Further, the separation device may be a membrane separator, such as a spinning membrane separator, or may be a centrifugal separation device.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A single-use fluid circuit for processing a fluid including a suspension of biological cellular components comprising:
   a) a container for the suspension of biological cellular components including an access port;
   b) a separation device for retaining selected biological cellular components and allowing other biological cellular components of said fluid to pass therethrough;
   c) a flow path connecting the container to the separation device defined by a tubing connected to the access port of the container that, when mounted on an associated fluid processing device, is routed vertically downwards from the container and then directed generally laterally toward the separation device, the container being configured, when in use, to be positioned so that gravity tends to flow fluid through the flow path; and
   d) the flow path having a first segment adjacent to the access port of the container, a second segment immediately downstream from the first segment and extending vertically downwardly therefrom, and a third segment immediately downstream from the second segment and extending laterally therefrom for engagement with a pump associated with the separation device, the first segment having a permanent, fixed configuration including a positive slope, so that biological cellular components moving through the first segment are subjected to a gravitational force tending to impede movement of said biological cellular components through the first segment and into the second and third segments.

2. The single-use fluid circuit of claim 1 in which the first segment of the flow path adjacent to the access port has a generally circular permanent, fixed configuration.

3. The single-use fluid circuit of claim 1 in which the first segment of the flow path adjacent to the access port has a generally S-shaped permanent, fixed configuration.

4. The single-use fluid circuit of claim 1 in which the permanent, fixed configuration of the first segment of the flow path is maintained by an adhesive.

5. The single-use fluid circuit of claim 1 in which the permanent, fixed configuration of the first segment of the flow path is maintained by a clamp.

6. The fluid circuit according to claim 1 in which the separation device is a membrane separator.

7. The fluid circuit of claim 6 in which the separation device has a spinning membrane.

8. In a procedure for processing a fluid including a suspension of biological cellular components to be separated utilizing a single use fluid circuit comprising a container for the fluid including an access port connected by a flow path to a separation device defined by a tubing having a first segment connected to the access port of the container, a second segment immediately downstream from the first segment that is routed vertically downwards from the first segment, and a third segment immediately downstream from the second segment and extending generally laterally toward the separation device for engagement with a pump, the flow path being configured to be selectively draw fluid through the tubing, a method for reducing the accumulation of cellular material in the tubing during time periods when the procedure is interrupted, the method comprising:

providing the first segment of the flow path adjacent to the access port of the container with a permanent, fixed configuration, so that when it is mounted to the separation device, the segment has a positive slope, so that cellular components moving through the segment are subjected to a gravitational force tending to impede movement of said cellular components through the first segment and into the second and third segments.

9. The method of claim 8 further comprising providing the first segment of the flow path with a generally circular permanent, fixed configuration.

10. The method of claim 8 further comprising providing the first segment of the flow path with a generally S-shaped permanent, fixed configuration.

11. The method of claim 9 further comprising maintaining the permanent, fixed configuration of the first segment of the flow path with an adhesive.

12. The method of claim 9 further comprising maintaining the permanent, fixed configuration of the first segment of the flow path with a clamp.

* * * * *